United States Patent [19]

Witt

[11] Patent Number: 4,810,652
[45] Date of Patent: Mar. 7, 1989

[54] CELL GROWTH HARVESTER FOR ROLLER BOTTLES

[75] Inventor: Donald J. Witt, Cary, N.C.

[73] Assignee: Becton, Dickinson and Company, Franklin Lakes, N.J.

[21] Appl. No.: 143,480

[22] Filed: Jan. 13, 1988

[51] Int. Cl.[4] .............................................. C12M 1/38
[52] U.S. Cl. ................................. 435/296; 435/285; 15/211; 215/1 C; 215/1 R
[58] Field of Search ............... 435/296, 285, 310, 287, 435/261; 47/1-4; 220/90; 134/166 C, 192; 215/1 C, 1 R, 329; 15/395, 401, 72, 93 R, 104.05, 104.1 C, 104.16, 236.01, 236.02-236.10, 236 R, 246.5, 212, 211, 213

[56] References Cited

U.S. PATENT DOCUMENTS

| | | | |
|---|---|---|---|
| 3,116,576 | 1/1964 | Block | 15/211 X |
| 3,702,806 | 11/1972 | Oliva | 435/296 X |
| 3,812,016 | 5/1974 | Muller et al. | 195/139 |
| 3,853,712 | 12/1974 | House et al. | 195/127 |
| 3,941,661 | 3/1976 | Noteboom | 195/127 |
| 3,948,732 | 4/1976 | Haddard | 435/285 |
| 4,004,981 | 1/1977 | Hurni et al. | 195/127 |
| 4,065,359 | 12/1977 | Hurni | 15/236.06 |
| 4,238,568 | 12/1980 | Lynn | 435/296 X |
| 4,317,886 | 3/1982 | Johnson et al. | 435/285 |
| 4,377,639 | 3/1983 | Lee | 435/285 |
| 4,556,639 | 12/1985 | Isawa et al. | 435/284 |
| 4,600,694 | 7/1986 | Clyde | 435/312 |

OTHER PUBLICATIONS

Bellco Biotechnology Catalog (BGE-6), p. 117, Bellco Glass Inc., Vineland, N.J.

Primary Examiner—Larry Jones
Attorney, Agent, or Firm—Robert P. Grindle

[57] ABSTRACT

A harvester is provided for mechanically removing cells from the internal surfaces of conventional, unmodified roller bottles. The device is a foldable, flexible arrangement which may be inserted into the neck openings of conventional roller bottles, without any, or only minor, modification thereof. Once inserted, the device of the invention mechanically expands to engage the internal surface of the bottle for the scraping thereof as the bottle revolves, thus effectively removing the cell growth rapidly and without the tedium of laborious hand scraping.

5 Claims, 4 Drawing Sheets

CELL GROWTH HARVESTER FOR ROLLER BOTTLES

BACKGROUND AND DESCRIPTION OF THE INVENTION

The present invention relates to a roller bottle for cell growth and production, and more particularly, concerns a device for scraping the grown or cultured cells from the internal surface of the roller bottle in order to achieve enhanced harvesting of cells so grown.

Containers which are used in the laboratory in like situations for culturing of cells are commonly known as "roller bottles." These roller bottles are generally cylindrically shaped and are adapted to rotate about their axes. The interior surfaces of such roller bottles are for providing active surfaces for cells. A liquid growth medium is introduced into the roller bottle. The rotating movement of the bottle keeps the internal surfaces wetted with the liquid medium, thereby encouraging the growth of cells. Rotating rollers in an appropriate apparatus are employed to rotate these rollers. Usually, the roller bottle apparatus is adapted to be placed inside an incubator or incubating room to control the temperature of cell growth inside the roller bottles.

It is desirable to grow large amounts of cells, mostly for cell by-products, such as pharmaceutical substances that are secreted by cells; for example insulin, interferon, urokinase or viral vaccines. Standard roller bottles have been successful in increasing the yield of cell growth in as much as the entire inside peripheral surface area can be utilized for cell culturing.

In conceiving ways to increase the yield of growing cells in roller bottles, there are substantial constraints which have to be considered in suggesting improvements. In particular, roller bottle rotation devices are widely used in standard sizes and incubators. These devices are in place in many laboratories and are designed to accept roller bottles of a specific size and shape. Thus, to replace these would be expensive and cause substantial lack of standardization throughout the laboratory field. Thus, the outside configuration or diameter of roller bottles is generally not one of the parameters which is changed to improve the yield of cells grown in roller bottles. Accordingly, improvements in roller bottles for increasing cell growth, for practical purposes, is limited to modifications of interior surfaces of the roller bottle, and/or improvements in harvesting the cells once they are grown.

Various approches have been used in order to increase the surface area internally of roller bottles. One approach is to increase the amount of actual surface available for cells to grow on. Representative of prior art devices which increase the surface area internally of conventional roller bottles are U.S. Pat. Nos. 3,941,661 issued Mar. 2, 1976 and 4,317,886 issued Mar. 2, 1982.

Another approach to increasing the yield of cells developed internally of roller bottles includes the combination of increasing the surface area thereof, and the use of involved mechanical devices cooperating with these increased surfaces in order to remove a greater harvest of cells once they are developed on the increased surface internally of the bottles. Representative of these devices include those taught and claimed in U.S. Pat. Nos. 4,004,981 issued Jan. 25, 1977; 4,065,359 issued Dec. 27, 1977 and 4,600,694 issued July 15, 1986. While each of the above three patents have the effect of increasing the surface area internally of roller bottles and increasing the yield of cells removed therefrom, the internal devices utilized in these patents and the arrangements for scraping the cells from the increased surface areas are very involved and, increase the cost of roller bottles, and the product derived therefrom, substantially. Moreover, these are not single-use devices and have been used largely in the labs where they originated.

One arrangement, of course, utilized frequently in past procedures for removing cells from the internal surface of conventional roller bottles is simply the use of a scraper device in the form of a flat thin structure similar to a knife positioned at the end of a rod which a lab technician utilizes to manually scrape in a tedious manner the cells which have developed on the internal surface of a roller bottle.

An additional approach to cell removal is by other than mechanical means. Representative of these include U.S. Pat. No. 4,556,639 issued Dec. 3, 1985 which utilizes an inertial force in order to remove cells formed on the internal surface of bottles. U.S. Pat. No. 3,853,712 issued Dec. 10, 1984 uses the shearing action of fluid in order to remove cells or alternatively the use of an enzyme for removing cells. This patent teaches the combination of these two approaches, as well. A further approach includes that taught and claimed in U.S. Pat. No. 3,812,016 which teaches the use of sand or other granulate matter for physically removing the cells from the internal surface either alone or in combination with a shearing action from liquids.

With this invention, by contrast, an arrangement for mechanical removal of cells grown on the internal surface of roller bottles is provided with a device which may be folded so that it may be slipped through the neck of a conventional roller bottle. The folding of the device, in accordance herewith, is of flexible blades which, when they move past the neck of the roller bottle and into the bottle itself, spring back into their initial position so that the blades move against the internal surface of the roller bottle. Thereafter, the scraper blades are rotated, in accordance herewith, to scrape mechanically all of the cells which have formed on the internal surface of the roller bottle. In addition, the weight of the scraper and the differential rotation of the scraper and the bottle generates a functional force enhancing the scraping action.

With this arrangement, of course, the roller bottle itself does not need to be modified in any way in order to provide the scraping action in accordance herewith. As a consequence, the same roller bottles and roller apparatus is utilized without any expensive modifications.

An alternative embodiment of the device herein includes precise mechanical spreading of the blades of the scraper device prior to the placing of the roller bottle onto the roller apparatus. In this way, a more precise engagement of the internal surfaces of the roller bottle is provided with this embodiment.

Finally, an embodiment of the invention is provided which is the most simple and least expensive device provided in accordance with this invention. This embodiment includes the blades for engaging the internal surface in the same manner as discussed above with the previous embodiments, but this particular embodiment requires a roller bottle that has a removable top so that the fins or blades of the scraper apparatus may be inserted. This is the only modification and the scraper apparatus is extremely simple and inexpensive of construction.

Other objects and advantages of this invention will be apparent from the following description, the accompanying drawings and the appended claims.

DETAILED DESCRIPTION OF THE INVENTION

Figure 1:
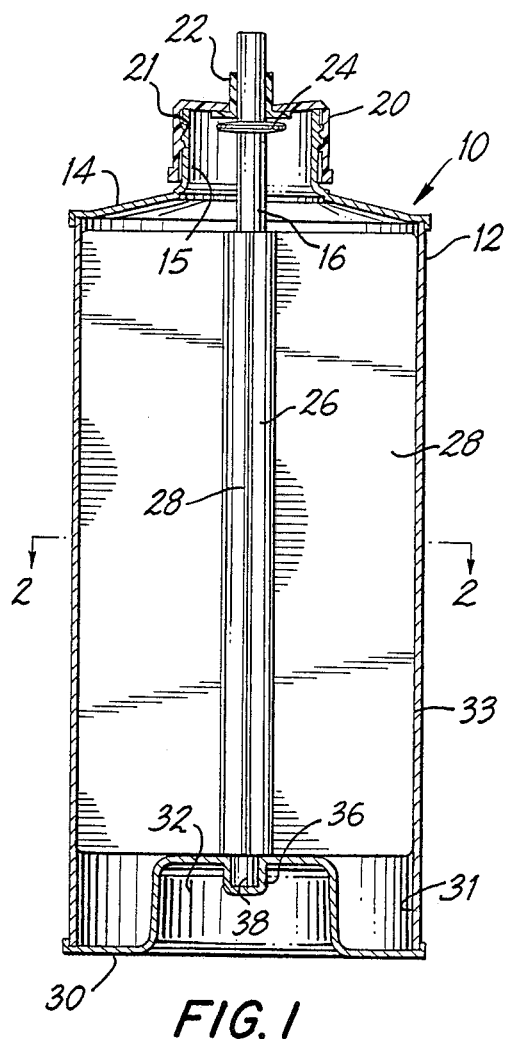
FIG. 1 is a longitudinal sectional view of a conventional roller bottle having disposed therein one embodiment of scraper apparatus illustrating the invention.

Referring to the drawings in which like reference characters refer to like parts throughout the several views thereof, FIG. 1 shows the roller bottle assembly of the invention generally designated by the reference number 10, which includes a roller bottle 12 constructed in a conventional manner. That is, roller bottle 12 includes a permanently affixed top 14 which includes a standard neck 15 for roller bottle 12.

The opposite base end of roller bottle 12 shown in FIG. 1 includes an end or base cap 30 with a central annular indentation 32 formed adjacent the axis of the roller bottle. Usually, the indentation 32 may be utilized as a manner in which bottles may be stacked for storage purposes. Thus, indentation 32 receives an adjacent neck 15 of another roller bottle. The cap or top 14 and the base 30 may be joined to the annular wall of bottle 12 by heat lamination or by adhesives, as practitioners-in-the-art will understand.

Figure 2:
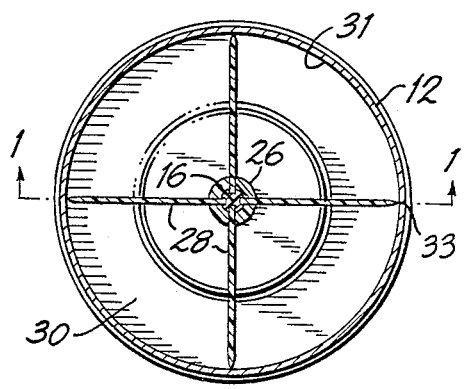
FIG. 2 is a sectional view of the device of FIG. 1 taken along lines 2—2 of FIG. 1.

The top of neck 15 includes screw threads 24 for receiving, in the usual manner, a closure for neck 15. However, in the arrangement shown in FIG. 1, the closure has been removed so as to utilize the screw threads 24 for receiving a cap 20 which accommodates the bushing 22 for a shaft 16 of the scraper apparatus of the invention. Shaft 16 has, in turn, mounted coaxially thereof, a weight arrangement 26 which serves to provide sufficient "body" for the scraper apparatus of the invention during the rotation thereof for scraping the internal surface 31 of bottle 12 to remove cells formed thereon. Shaft 16 includes a plurality of blades 28 mounted thereon. As shown in FIG. 2, four such blades are mounted on shaft 16. However, it will be understood that a larger or smaller number of flexible blades 28 may be included or mounted on shaft 16.

Figure 3:
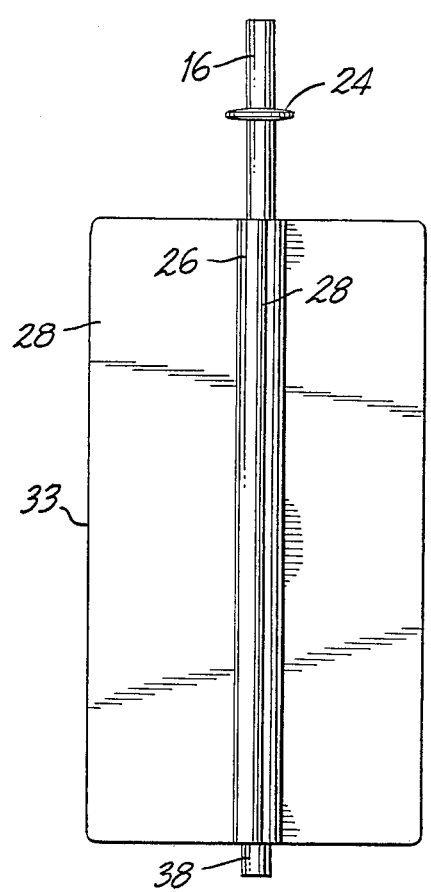
FIG. 3 is a side elevational view of the scraper assembly alone of FIG. 1 removed from the roller bottle.
Figure 4:
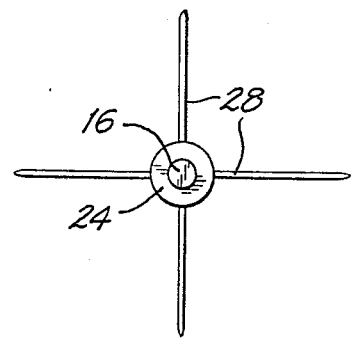
FIG. 4 is a top plan view of the scraper assembly of FIG. 3.

As can be seen in FIGS. 3 and 4, showing the scraper apparatus alone, the lower end of shaft 16 includes an extension 38 which is received in a pocket 36 in bottom wall 30 of the bottle 12. Thus, the part 38 serves to seat the scraper and position it centrally and coaxially with bottle 12 during the rotation of the scraper apparatus in bottle 12 for scraping cells from the internal surface 31 of bottle 12.

The upper end, as viewed in FIGS. 1 and 3, of shaft 16 includes a bushing 22 which is received in the scraper assembly cap 20. Bushing 22 serves as the surface at the upper end of shaft 16 allowing rotation of shaft 16 relative to bottle 12. An abutment 24 is fixed on shaft 16 to prevent shaft 16 from "riding-up" in bushing 22 during the rotation thereof.

Figure 5:
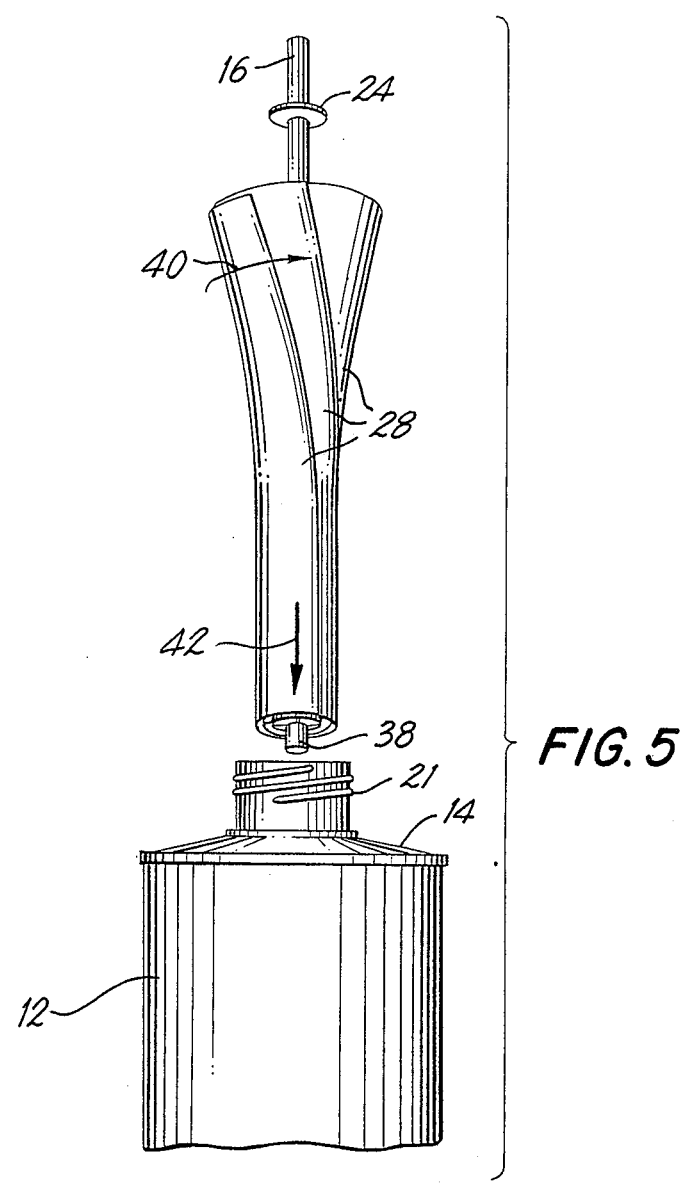
FIG. 5 is a somewhat diagramatic illustration of the scraper apparatus of FIG. 1 with the blades thereof folded for insertion through the neck of a conventional roller bottle.

Referring now to FIG. 5, the scraper assembly is shown with the blades 28 folded around shaft 16. With the arrangement, the entire scraper assembly is of small enough diameter to be received through neck 15 of bottle 12. Once insertion is made, wrapped flexible blades 28 spring open so that the outer edges 33 thereof engage surface 31. The bottom portion 38 of shaft 16 is positioned in place in the pocket 36 in the bottom surface 30 of bottle 12. The cap 20 of the assembly, with the accommodating bushing 22, is placed on top of bottle 12 so that the assembly is in place for rotation within bottle 12 for removing the cells formed on the internal surface of bottle 12.

In this connection, after the usual formation of cells with the roller bottle 12 rolling in the proper environment for the formation of the cells, the procedure utilized with the invention herein is to remove the roller bottle with the formed cells on the walls thereof from the conventional roller apparatus. The cell forming liquid media remaining in the roller bottle may be decanted from the bottle, and a small amount of saline solution added to prevent the cells from "drying." Alternatively, the liquid media may remain if it is only a small amount. Thereafter, the scraper apparatus of the invention, as described above, is inserted through the neck of the bottle and the cap therefor with the appropriate accommodating bushing is placed on the open neck of the bottle. Thereafter, the cells are loosened from the internal surface 31 of the roller bottle by the scraper apparatus of the invention being rotated in the bottle, and by the flexible blades 28 moving against the internal surface of the bottle for removing cells. Thereafter, the cells are washed down by a fluid suspension and poured from the flask by removing the suspension containing the cells therein.

Figure 6:
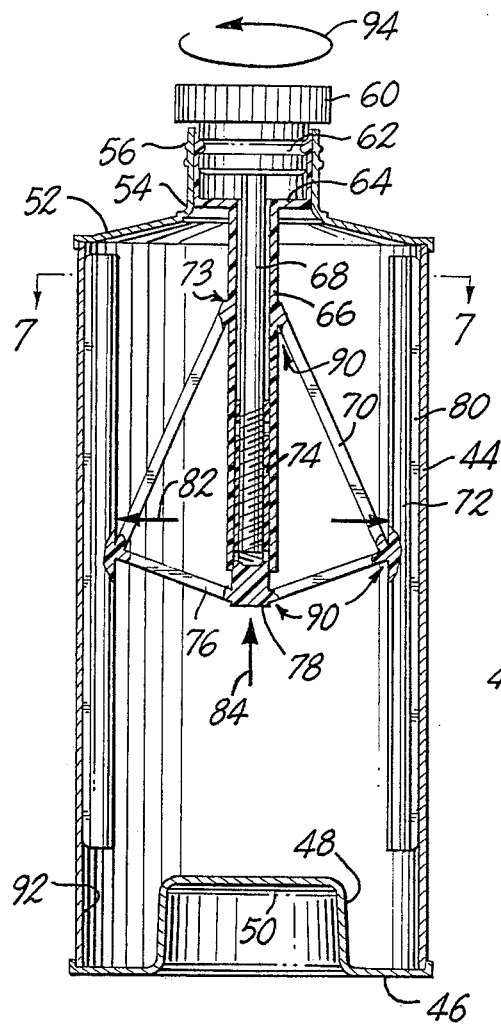
FIG. 6 is a longitudinal sectional view of a conventional roller bottle with a further embodiment of scraper apparatus of the invention inserted therein.
Figure 8:
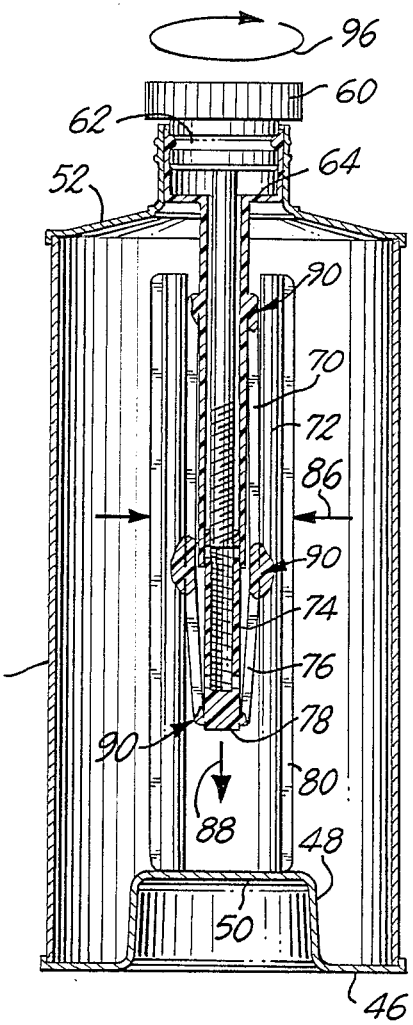
FIG. 8 is a longitudinal sectional view of the device of FIG. 6 shown in a different position.
Figure 7:
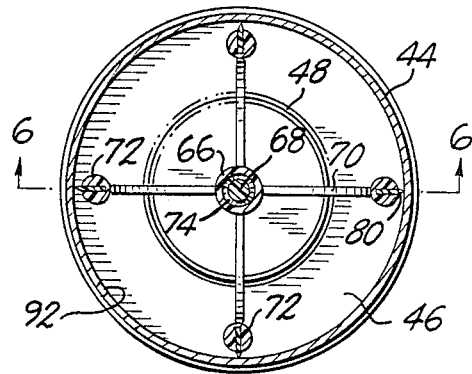
FIG. 7 is a sectional view of the roller bottle of FIG. 6 taken along lines 7—7 of FIG. 6.

Referring now to FIGS. 6, 7 and 8, a further embodiment of the invention is shown. In this embodiment, the flexible scraper is opened and closed by a mechanical twist and linkage arrangement, with an operating knob 60 extending from the open neck of the bottle for being rotated to cause the blades to move from a central coaxial position in a roller bottle with a drive shaft for the scraper apparatus, into an extended engaging position against the internal surface of the roller bottle.

Thus, as can be seen in FIG. 6, a bottle 44 is shown having a cap or cooperating top 52 fixed in place on the top thereof and a bottom end wall 46 with the usual coaxial indentation 48 formed therein. The top wall or cap 52 of bottle 44 includes a neck 54 having external threads 56 for receiving the closure for the top of the bottle when it is in use and being rotated on roller apparatus for forming cells on the internal surface 92 thereof. In the figures shown of this embodiment, however, the usual closure has been removed so that the scraper assembly of the invention can be inserted through neck 54. Thus, actuating knob 60 includes a lower portion 62 thereof for being received in neck 54 of bottle 44. Fixed on portion 62 is a shaft 68 which rotates with knob 60.

Included with the scraper assembly of this embodiment is a cup-shaped fixed well 64 which receives the rotating lower portion 62 of operating knob 60. Extending from the cup-shaped well 64 is a fixed annular extension 66 for receiving in cooperating rotational movement the shaft 68. Positioned between the fixed annular shaft 66 and the rotatable shaft 68 and coaxially positioned therein are cooperating screw threads which serve to actuate a movable bushing 74 therebetween, which, in turn, moves in the direction of arrows 84, 88 upwardly, or downwardly, depending upon the direction of rotation of the knob 60, as shown by the rotational arrows 94, 96.

Thus, movement upwardly as indicated by the arrow 84 is accomplished by rotation in the direction 94 shown in FIG. 6, while movement downwardly as indicated by arrow 88 in FIG. 8 is accomplished by rotation in the direction as indicated by arrow 96 in FIG. 8. Positioned on the bottom of movable bushing 74 and movable therewith is a linkage arm connection 78. One end of lower linkage arms 76 is connected to 78. The opposite end is connected to one of weights 72, as shown in FIG. 7. Also, as shown in FIG. 7, each of the weights 72 is a vertically extending weight having disposed on the outer edge thereof a blade 80 for engaging the internal surface 92 of bottle 44. Separate upper arms or linkages 70, as shown in FIG. 6, extend from weights 72 to a fixed position 73 on fixed annular shaft 66. As can be seen in FIG. 6, the upper linkages or arms 70 and the lower linkages or arms 76 form a plurality of living hinges 90 in their connection with the lower portion 78 of movable bushing 74 and the weights 80. FIG. 7 shows the extended position of upper arms or linkages 70 relative to the respective weights 72 and blades 80 positioned on the outer edges thereof.

Thus, as shown in FIG. 6, rotation of knob 60 in the direction of arrow 94 causes the arms or linkages 70, 76 to move the weights and associated blades 72, 80 outwardly against or into engagement with the internal surface 92 of bottle 44.

In the opposite direction of rotation of knob 60 as shown by arrow 96 in FIG. 8, the linkage arrangement shown in FIG. 6 moves in the direction of arrows 86 to a coaxial folded position as shown in FIG. 8. In this position, the entire device may be withdrawn from bottle 44 through neck 54 thereof. As can be seen in FIG. 8, the scraper assembly rests on the raised platform surface 50 of indentation 48, in the position shown in FIG. 8. In the position shown in FIG. 6, the entire assembly is held by frictional fit with the cup-shaped fixed well 64 engaging the internal surface of neck 54.

Figure 9:
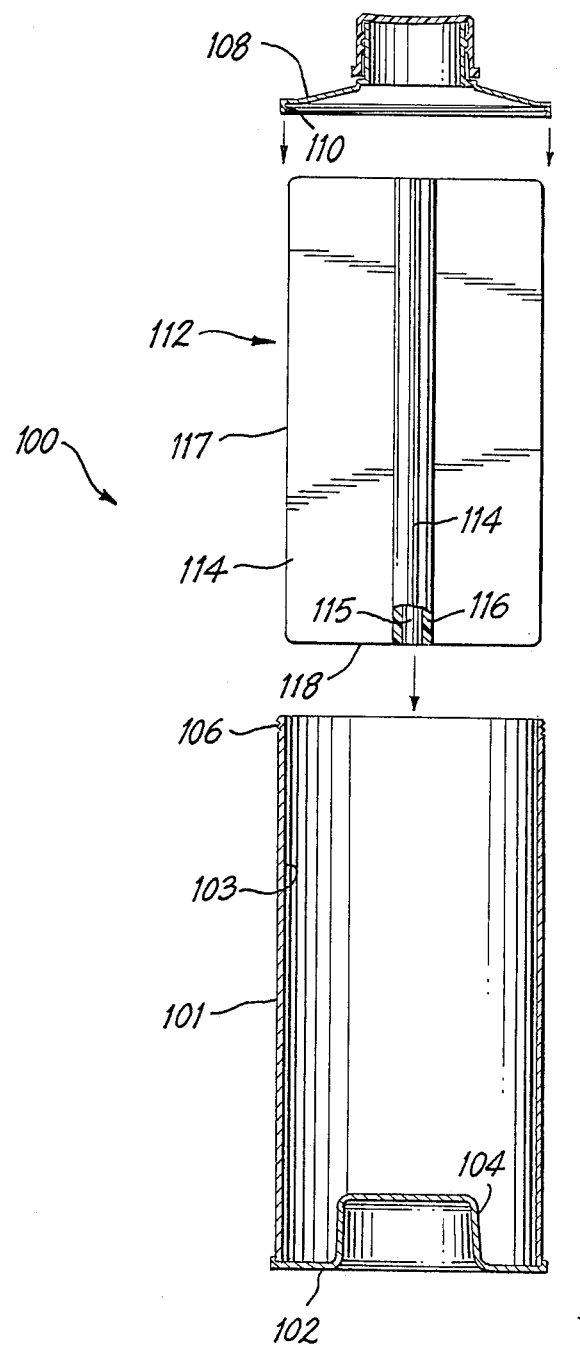
FIG. 9 is an exploded view of a further embodiment of cell scraper apparatus positioned in a roller bottle and illustrating the invention.

Referring now to FIG. 9, an exploded view of an additional embodiment of flexible scraper apparatus of the invention is shown. In this embodiment, the assembly 100 includes a roller bottle 101 modified to a certain extent from that shown in the other two embodiments described above. That is, in this embdiment, the cap or top 108 of bottle 106 is modified to be removable from bottle 101. Thus, top 108 includes a female thread 110 cooperating with a male thread 106 on the top edge of bottle 101.

In this arrangement, the scraper assembly 112 is a simplified arrangement mounted on a central axially aligned shaft 115 having a plurality of weights 116 positioned thereon in spaced relationship around the circumference of shaft 115 in the same manner as the weights positioned in the embodiment shown in FIGS. 1-5, described above. Extending from weights 116, in the same manner as the embodiment shown in FIGS. 1-5, are a plurality of flexible blades 114.

As can be seen in FIG. 9, bottle 101 includes the usual coaxial indentation 104 in the surface of the bottom wall 102 thereof. Thus, when the scraper assembly 112 is inserted in bottle 101, the bottom surface 118 thereof rests and rotates on the raised surface of indentation 104.

In view of the fact that no folding action is required with this particular embodiment, te scraper assembly is merely inserted into the roller bottle 101 so that the outer edges 117 of blades 114 engage the internal surface 103 of bottle 101 for rotating thereagainst and removing cells already formed on the surface 103.

Thus, as will be appreciated from the above, there is provided in accordance with this invention a scraper assembly for insertion into a conventional roller bottle for removing precisely all of the cells grown or formed on the internal surface thereof in an efficient rapid manner.

This is achieved by a simple apparatus of uncomplicated features inexpensively manufactured and handled. The assembly is comprised of multiple parts which can be mass produced, as will be understood, from a variety of materials including such thermoplastics as polyethylene and polypropylene. Materials will be selected which will provide a degree of resiliency for the purposes provided of relative flexible movement where required for the foldable assembly of the invention herein and which materials can be sterilized. Also, as will be understood, the resiliency of the scraper blades of the assembly is important for providing a complete clean removal of the cells from the internal surface of the roller bottle.

While the forms of apparatus herein described constitute preferred embodiments of the invention, it is to be understood that the invention is not limited to these precise forms of apparatus and that changes may be made therein without departing from the scope of the invention which is defined in the appended claims. For example, where each of the embodiments shown describe an extended arm and/or blade assembly for engaging the internal surface of roller bottles in which four such extendable blades are shown, it will be understood that a greater or lesser number of blades may be utilized for achieving the scraping action required in accordance with the assembly herein.

What is claimed is:

1. A harvester device for cell removal from the internal surface of roller bottles, characterized by
 (a) a hollow cylindrical roller bottle body forming a hollow chamber;
 (b) said hollow cylindrical body having a substantially open end and a closed end;
 (c) said substantially open end having a coaxially arranged neck portion forming the open portion of said substantially open end;
 (d) an insertable scraper assembly for insertion through said neck and for engaging the internal surfaces of said hollow cylindrical body;
 said scraper assembly comprising
  (1) an elongated shaft with a first end and a second end;

(2) a plurality of weights positioned circumferentially around said shaft for imparting body to said scraper assembly;

(3) said plurality of weights being elongated and extending from a point adjacent said first end to a point adjacent said second end;

(4) an elongated flexible foldable scraper blade positioned on each of said weights; and (e) each said scraper blade being foldable against said shaft for insertion through said neck whereby after insertion each said blade unfolds so that the outer edge thereof engages the internal surface of said hollow cylindrical body, (f) said closed end of said hollow cylindrical body includes a coaxially positioned pocket; and (g) the second end of said elongated shaft includes an extension for insertion and rotation in said pocket.

2. The device of claim 1, further characterized by (a) said scraper assembly includes a cap for fitting over the open end of said neck portion;

(b) a bushing fixed in said cap; and (c) said first end of said elongated shaft being mounted for rotation in said bushing.

3. A scraper assembly for scraping the internal surface of roller bottles free of cultured cells formed thereon, characterized by (a) an elongated shaft with a first end and a second end;

(b) a plurality of elongated weights positioned circumferentially around said shaft for imparting body to said scraper assembly;

(c) each said elongated weight extending from a point adjacent said first end to a point adjacent said second end;

(d) an elongated flexible blade mounted on and extending along each said weight; and (e) whereby when said scraper assembly is inserted into a roller bottle and rotated, the edge of each blade opposite said weight engages the internal surface of a roller bottle and scrapes off the cultured cells formed thereon;

(f) said elongated shaft includes an elongated rotatable portion and an elongated fixed portion with said rotatable portion rotatable coaxially in said fixed portion;

(g) an operating knob positioned on said first end of said rotatable portion of said shaft for causing engagement of said blades with the internal surface of a roller bottle in which said assembly is inserted and for causing said blades to move around the internal surface for removing cells.

4. The assembly of claim 3, further characterized by (a) cooperating bushing means vertically movable between said shaft rotatable portion and said shaft fixed portion;

(b) a plurality of first linkage means mounted between said fixed portion of said shaft and said weights;

(c) a plurality of second linkage means mounted between said vertically movable bushing means and said weights; and (d) whereby rotation of said shaft in one direction causes said blades and weights to move against said shaft for insertion into a roller bottle, and rotation in the opposite direction causes said blades and weights after insertion to flex outwardly on said first and second linkage means to engage the internal surface of a roller bottle in which said assembly is inserted.

5. The assembly of claim 3, further characterized by (a) each said flexible blade is foldable around said shaft for allowing receipt of said assembly through the neck of a roller bottle.

* * * * *